(12) United States Patent
Polin et al.

(10) Patent No.: US 9,956,372 B2
(45) Date of Patent: May 1, 2018

(54) TRACHEAL HUMIDIFICATION DEVICE

(71) Applicant: Phillip Polin, Corning, CA (US)

(72) Inventors: Phillip Polin, Corning, CA (US);
Audrey Chikalla, Bangor, CA (US)

(73) Assignee: Phillip Polin, Corning, CA (US)

( * ) Notice: Subject to any disclaimer, the term of this patent is extended or adjusted under 35 U.S.C. 154(b) by 0 days. days.

(21) Appl. No.: 15/065,545

(22) Filed: Mar. 9, 2016

(65) Prior Publication Data

US 2016/0263342 A1 Sep. 15, 2016

Related U.S. Application Data

(60) Provisional application No. 62/130,143, filed on Mar. 9, 2015.

(51) Int. Cl.
| | |
|---|---|
| *A61M 16/16* | (2006.01) |
| *A61M 11/02* | (2006.01) |
| *A61M 16/10* | (2006.01) |
| *A61M 16/08* | (2006.01) |
| A61M 16/04 | (2006.01) |
| A61M 11/06 | (2006.01) |
| A61M 11/04 | (2006.01) |

(52) U.S. Cl.
CPC .... *A61M 16/1045* (2013.01); *A61M 16/0833* (2014.02); *A61M 16/16* (2013.01); *A61M 11/044* (2014.02); *A61M 11/06* (2013.01); *A61M 16/0463* (2013.01); *A61M 16/0465* (2013.01); *A61M 16/109* (2014.02); *A61M 16/1055* (2013.01); *A61M 2202/0208* (2013.01); *A61M 2205/3368* (2013.01); *A61M 2205/7518* (2013.01)

(58) Field of Classification Search
CPC ............... A61M 16/16; A61M 16/109; A61M 16/1055; A61M 11/06; A61M 2202/0208; A61M 16/0465; A61M 16/0463; A61M 16/0833; A61M 16/1045
See application file for complete search history.

(56) References Cited

U.S. PATENT DOCUMENTS

| | | | | | |
|---|---|---|---|---|---|
| 4,951,661 | A | * | 8/1990 | Sladek | ............... A61M 16/0808 128/202.27 |
| 5,433,195 | A | * | 7/1995 | Kee | ....................... A61M 16/08 128/207.14 |
| 5,546,930 | A | * | 8/1996 | Wikefeldt | ............. A61M 16/08 128/201.13 |
| 5,775,325 | A | * | 7/1998 | Russo | ............... A61M 16/0463 128/202.27 |

(Continued)

*Primary Examiner* — Justine Yu
*Assistant Examiner* — Douglas Sul
(74) *Attorney, Agent, or Firm* — Maschoff Brennan

(57) ABSTRACT

Some embodiments of the invention include a tracheal humidification device. The tracheal humidification device may include a first body portion and a second body portion. The first body portion may include a tracheostomy connection port formed to couple with a tracheostomy connection tube; and a heat moisture exchanger port formed to couple with a heat moisture exchanger. The second body portion may be coupled with the first body portion, for example, rotatably coupled. The second body portion may include a nebulizer port formed to couple with a nebulizer and having a closable seal that is closable when the nebulizer is not coupled with the nebulizer port; and a suction port having a closable cap.

17 Claims, 7 Drawing Sheets

(56) References Cited

U.S. PATENT DOCUMENTS

| | | | |
|---|---|---|---|
| 6,318,368 B1 * | 11/2001 | Morejon | A61M 1/0078 128/202.28 |
| 6,579,254 B1 * | 6/2003 | McNary | A61M 16/0463 128/203.12 |
| 6,588,425 B2 * | 7/2003 | Rouns | A61M 16/0463 128/200.26 |
| 7,021,313 B1 * | 4/2006 | Crump | A61M 16/0463 128/207.14 |
| 7,263,997 B2 * | 9/2007 | Madsen | A61M 16/0463 128/200.26 |
| 2009/0235925 A1 * | 9/2009 | Power | A61B 17/3474 128/200.14 |
| 2010/0132706 A1 * | 6/2010 | Nashed | A61M 16/0078 128/203.28 |
| 2014/0014103 A1 * | 1/2014 | Smaldone | A61M 16/14 128/203.12 |
| 2015/0343164 A1 * | 12/2015 | Ritter, III | A61M 16/0816 128/200.14 |

* cited by examiner

TRACHEAL HUMIDIFICATION DEVICE

SUMMARY

Some embodiments of the invention include a tracheal humidification device. The tracheal humidification device may include a first body portion and a second body portion. The first body portion may include a tracheostomy connection port formed to couple with a tracheostomy connection tube; and a heat moisture exchanger port formed to couple with a heat moisture exchanger. The second body portion may be coupled with the first body portion, for example, rotatably coupled. The second body portion may include a nebulizer port formed to couple with a nebulizer and having a closable seal that is closable when the nebulizer is not coupled with the nebulizer port; and a suction port having a closable seal.

In some embodiments, the first body portion comprises a T-piece comprising a medial arm, a distal arm, and/or a proximal arm. In some embodiments, the tracheostomy connection port is formed with the proximal arm. In some embodiments, the heat moisture exchanger port is formed with the medial arm. In some embodiments, the distal arm is coupled with the second body portion.

In some embodiments, the second body comprises a T-piece comprising a medial arm, a distal arm, and a proximal arm. In some embodiments, the proximal arm is coupled with the first body portion. In some embodiments, the nebulizer port is formed with the medial arm. In some embodiments, the suction port is formed with the distal arm.

In some embodiments, the first body portion and the second body portion are rotatable relative to one another.

In some embodiments, the tracheal humidification device comprises a closed system when coupled with a heat moisture exchanger and/or a tracheostomy connection tube.

In some embodiments, the first body portion and the second body portion form a unitary body. In some embodiments, either or both the first body portion and the second body portion comprises a T-piece. In some embodiments, the nebulizer port comprises a spring-loaded valve. In some embodiments, the tracheal humidification device may include an oxygen inlet port.

In some embodiments, the tracheal humidification device may include a heat moisture exchanger removably coupled with the first body portion.

Some embodiments of the invention include a tracheal humidification device comprising a first T-piece and a second T-piece. In some embodiments, the first T-piece may include a first medial arm, a first distal arm, and/or a first proximal arm. In some embodiments, the first medial arm is formed to be removably coupled with a heat moisture exchanger. In some embodiments, the second T-piece may include a second medial arm, a second distal arm, and/or a second proximal arm. In some embodiments, the second proximal arm may rotatably coupled with the first distal arm. In some embodiments, the second medial arm may be formed to couple with a nebulizer. In some embodiments, the second distal arm may include a closable seal.

In some embodiments, the tracheal humidification device may include a heat moisture exchanger coupled with the first medial arm. In some embodiments, the tracheal humidification device may include an oxygen inlet port coupled with the heat moisture exchanger.

In some embodiments, the second medial arm comprises a spring-loaded valve. In some embodiments, the tracheal humidification device comprises a closed system when coupled with a heat moisture exchanger and/or a tracheostomy connection tube. In some embodiments, the first T-piece and the second T-piece form a unitary body.

Some embodiments of the invention include a tracheal humidification device that includes a first T-piece and a second T-piece. In some embodiments, the first T-piece may include a first medial arm, a first distal arm, and/or a first proximal arm. In some embodiments, the first proximal arm may be couplable with a tracheostomy connection tube. In some embodiments, the second T-piece may include a second medial arm, a second distal arm, and/or a second proximal arm. In some embodiments, the second proximal arm may be coupled with the first distal arm. In some embodiments, the second distal arm may include a removable cap. In some embodiments, the second medial arm may include a closable port configured to couple with a nebulizer. In some embodiments, the tracheal humidification device may include a heat moisture exchanger removably coupled with the medial arm of the first T-piece. In some embodiments, the tracheal humidification comprises a closed system when the first proximal arm is coupled with a tracheostomy connection tube, and the closable port is either closed or coupled with a nebulizer.

In some embodiments, the first T-piece and the second T-piece are rotatably coupled. In some embodiments, the tracheal humidification device may include an oxygen port coupled with the heat moisture exchanger. In some embodiments, the first T-piece and the second T-piece form a unitary body.

BRIEF DESCRIPTION OF THE FIGURES

These and other features, aspects, and advantages of the present disclosure are better understood when the following Disclosure is read with reference to the accompanying drawings.

DETAILED DESCRIPTION

Figure 1:
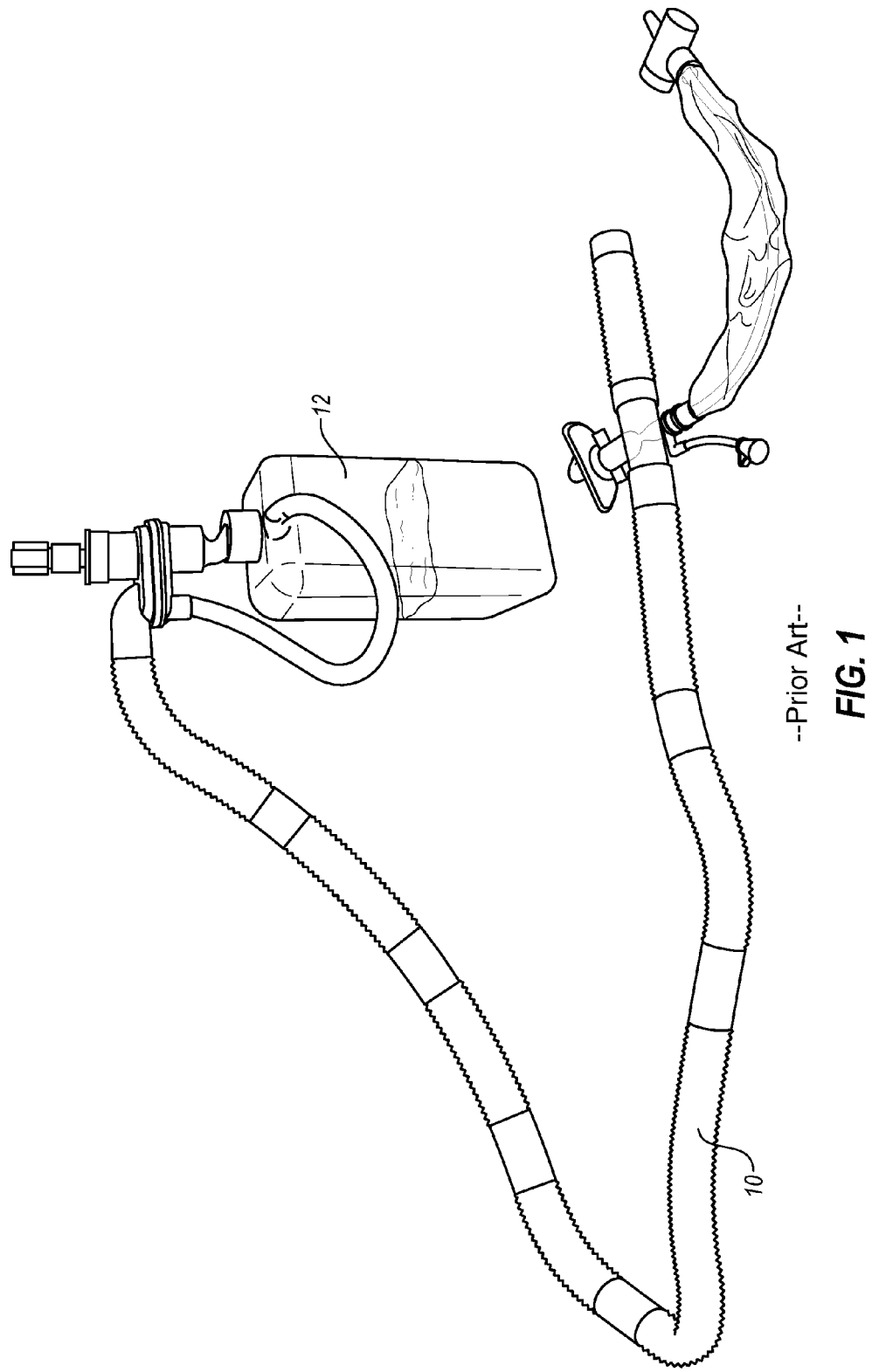
FIG. 1 is a perspective view of a conventional tracheal humidification device.
Figure 2:
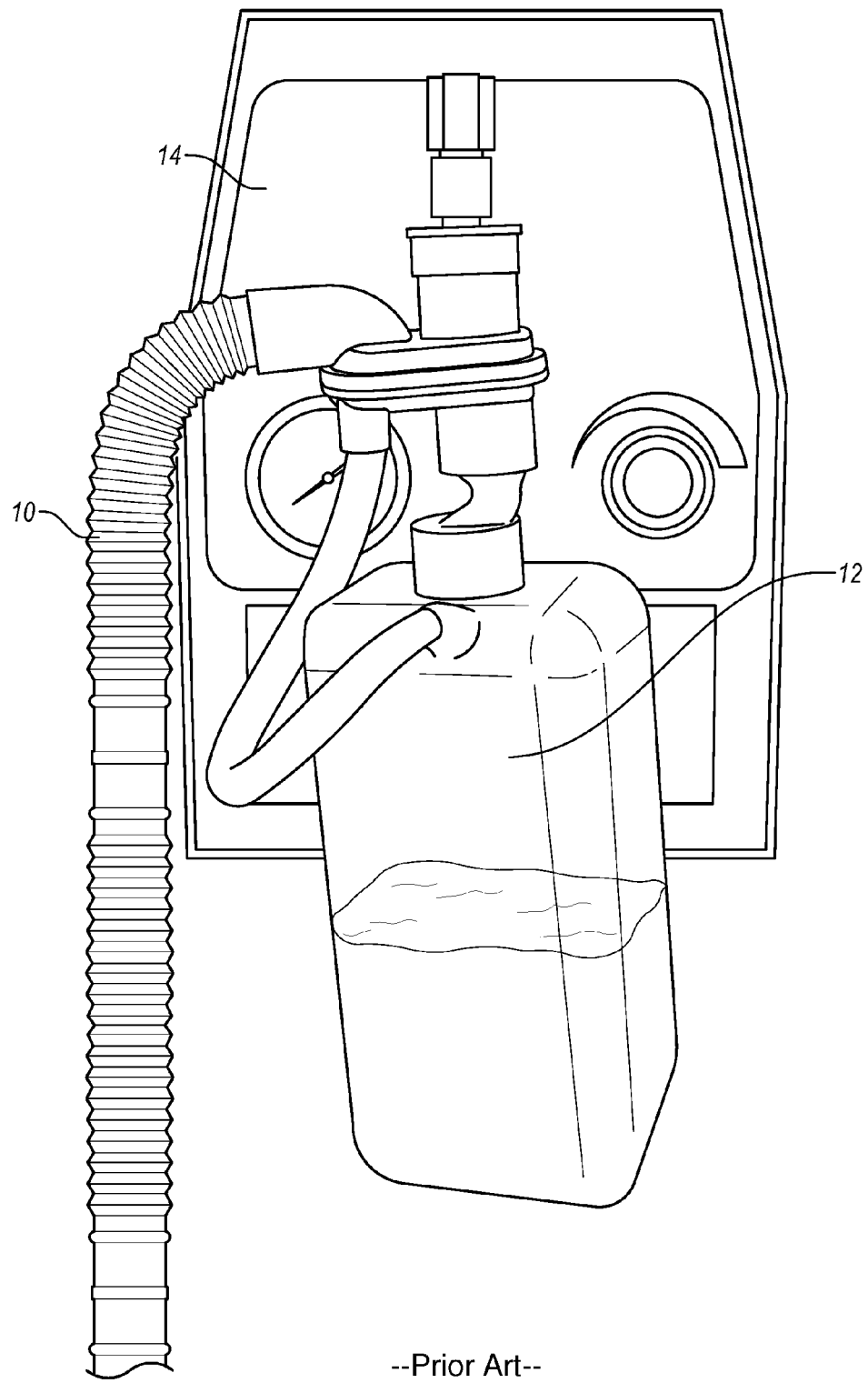
FIG. 2 is a perspective view of the tracheal humidification device of FIG. 1, attached to an air compressor.

The warming and humidifying functions of the nose and mouth are bypassed in patients with a tracheostomy; hence, patients with a tracheostomy may require supplemental humidification. Conventional tracheal humidification devices may include an air compressor that provides supplemental humidification. For example, with combined reference to FIGS. 1 and 2, one end of a hose 10 may be attached to the tracheostomy, and the other end of the hose 10 may be attached to a bottle 12 and/or an air compressor 14. The air compressor 14 may turn liquid in the bottle 12, which may include distilled water, into a mist that can be inhaled by a patient through the hose 10. After inhaling the mist or humidified air through the hose 10, the patient may exhale through the hose 10. Air compressors 14 may be used predominately in home settings or older care facilities.

Instead of using air compressors 14, more modern care facilities may deliver compressed air to the patient using a piping system and a flow meter coupled to the hose 10.

Some tracheal humidification devices may be open to ambient air, and the patient may inhale unfiltered ambient air through the hose 10. Since the filtering functions of the nose are bypassed in patients with a tracheostomy, patients with a tracheostomy lack means to filter the air themselves, and inhalation of this ambient air can be particularly detrimental such as, for example, by causing infection, inflammation, etc. Further, when the patient exhales through the hose 10 and into the ambient air, healthcare workers, family, and friends may be exposed to the patient's unfiltered air and secretions.

Even in more modern facilities where the filtered air may be delivered to the patient through the piping system and the flow meter coupled to a tracheostomy humidification device, there may be instances when the patient inhales unfiltered ambient air. For example, if the patient inhales at a force greater than the force of the filtered air being delivered to the patient through the hose 10, it may be possible for the patient to inhale unfiltered air.

Also, ambient air inhaled through some tracheal humidification devices may not be warmed. Since the warming functions of the nose are also bypassed in patients with a tracheostomy, this lack of warming of the air can be harmful to the patient. Some tracheal humidification devices may incorporate an electric heating rod in the bottle 12 to create a heated mist. Care must be taken, however, so that the bottle 12 does not go dry, which could melt the bottle 12 that may be plastic. Also, many of these heating rods do not have automatic shut-offs, and this could be a potential fire hazard. Heated mist may also be delivered by wrapping a heater unit around a top of the bottle 12. However, a thermometer may be required to ensure the heated mist does not get too hot. Heating the mist that is delivered to the patient may also raise the temperature of the room, which may make the patient uncomfortable.

Additionally, some tracheal humidification devices may include an oxygen adapter for patients who require supplemental oxygen. The oxygen adapter may be used to bleed the oxygen into the mist using a standard oxygen system, such as, for example, an oxygen concentrator. Some tracheal humidification devices that include an air compressor and/or oxygen concentrator may be noisy, and the high noise levels may not provide a good environment of care.

Also, some tracheal humidification devices may require frequent draining to provide free airflow. For example, the hose 10 may comprise both a breathing pathway and a secretion pathway for bronchial secretions. High volumes of secretions associated with the tracheostomy may block the hose 10, making breathing more difficult. Frequent draining or suctioning of the hose to clear the secretions from the breathing pathway may be time-consuming and taxing.

In addition, heat moisture exchangers (HMEs) and hydroscopic condensing humidifiers (HCHs) have traditionally been used on mechanically ventilated patients to warm and humidify inspired gases and to filter dust or harmful substances contained in the air. However, HMEs and HCHs may have a tendency to clog with the secretions, and thus, are not typically used on naturally ventilated patients.

Furthermore, some tracheal humidification devices may be large, bulky, and/or restrictive to the patient. For example, some tracheal humidification devices may cover a substantial portion of the patient's chest and/or shoulders and may substantially inhibit the patient's movement. Also, some tracheal humidification devices may not allow simple, simultaneous combination with other devices, such as, for example, nebulizers that may administer medications, temperature monitors, carbon dioxide monitors, suction devices, HMEs, and/or supplemental oxygen devices. Further, some tracheal humidification devices may be difficult to clean and/or suction because of the shape, number of parts, and/or configuration of one or more components, which may promote infection. Further, it may be difficult to replace one or more components of some tracheal humidification devices because of the shape, number of parts, and/or configuration of the one or more components, which may also promote infection.

Some embodiments of the invention include a tracheal humidification device that may be a closed system, may include an HME, and/or may be a passive device. A closed system, for example, may include a system that is not open to the ambient air. A passive device, for example, may include a device that does not need an electrically powered device for operation. In some embodiments, a closed device may be coupled with an electrically powered device in some configurations for purposes other than for humidification.

Figure 3:
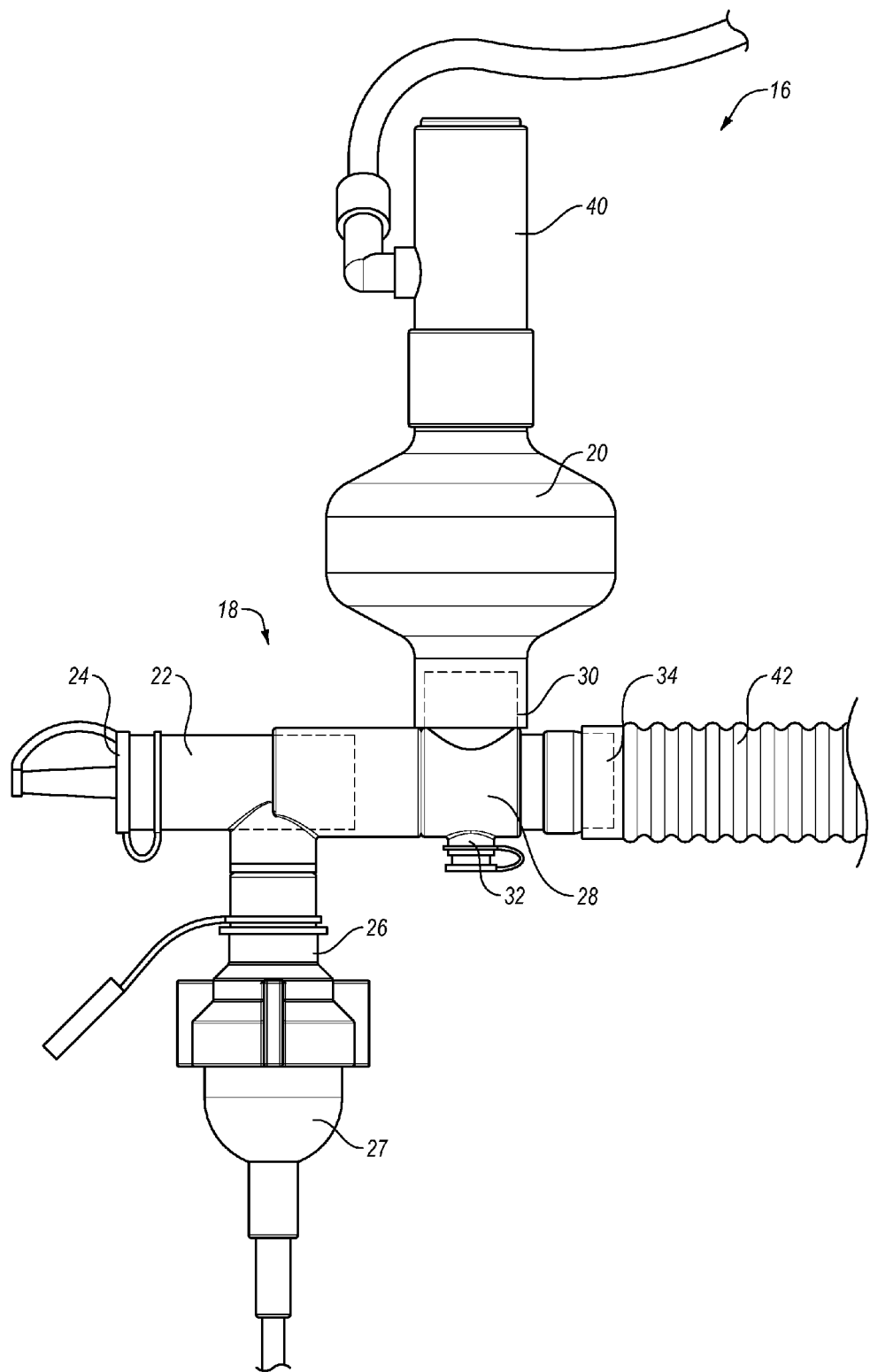
FIG. 3 is a perspective view of an example tracheal humidification device.

An example tracheal humidification device 16 is shown in FIG. 3. In some embodiments, the tracheal humidification device 16 may include a small number of parts and/or components, which may facilitate manufacturing, assembly, and/or replacement. In some embodiments, the tracheal humidification device 16 may include a body 18 and an HME 20 or similar device. In some embodiments, the body 18 of the tracheal humidification device 16 may comprise one or more generally T-shaped pieces, referred to hereinafter as "T-pieces." In some embodiments, two or more of the T-pieces may be coupled to each other by fitting, snapping, threading, connecting, attaching, fastening, or the like. Also, in some embodiments, the two or more T-pieces may also be integrally formed into a single piece. In some embodiments, one or more of the T-pieces may be rotatable with respect to each other. The body 18 may include any number of T-pieces. Further, the T-pieces may have other appropriate shapes, sizes, configurations, and arrangements, depending, for example, upon the intended use of the tracheal humidification device 16. In some embodiments, the T-pieces may be constructed of plastic or another suitable material that facilitates easy disposal and replacement.

In some embodiments, the body 18 may include one or more ports, such as, for example, a suction port 24, a nebulizer port 26, an HME port 30, a monitoring port 32, and/or a tracheostomy connection port 34. In some embodiments, one or more of the ports may include a removable cap and/or other removable seal, which may allow maintenance of a closed system in which all or substantially all ambient air entering the tracheal humidification device 16 is filtered through the HME 20.

In some embodiments, a distal end of the body 18 may include a first T-piece 22. In some embodiments, the first T-piece 22 may include the suction port 24 and/or the nebulizer port 26. In some embodiments, the suction port 24 may be disposed on a distal arm of the first T-piece 22 and may be generally perpendicular to the nebulizer port 26, which may be disposed on a medial arm of the first T-piece 22. In FIG. 3, the nebulizer port 26 is coupled with nebulizer 27. In some embodiments, a proximal end of the body 18 may include a second T-piece 28. In some embodiments, a proximal arm of the first T-piece 22 may be coupled to a distal arm of the second T-piece 28.

In some embodiments, the second T-piece 28 may include an HME port 30, a monitoring port 32, and/or a tracheostomy connection port 34. In some embodiments, the HME port 30 may be disposed on a medial arm of the second T-piece 28 and may be generally perpendicular to the tracheostomy connection port 34, which may be disposed on a proximal arm of the second T-piece 28. In some embodiments, the monitoring port 32 may be disposed on a body of the second T-piece 28.

The one or more ports of the tracheal humidification device 16 may have various configurations and arrangements on one or more T-pieces and/or the body 18. The body 18 may include additional or fewer ports than illustrated in connection with the tracheal humidification device 16.

Figure 4:
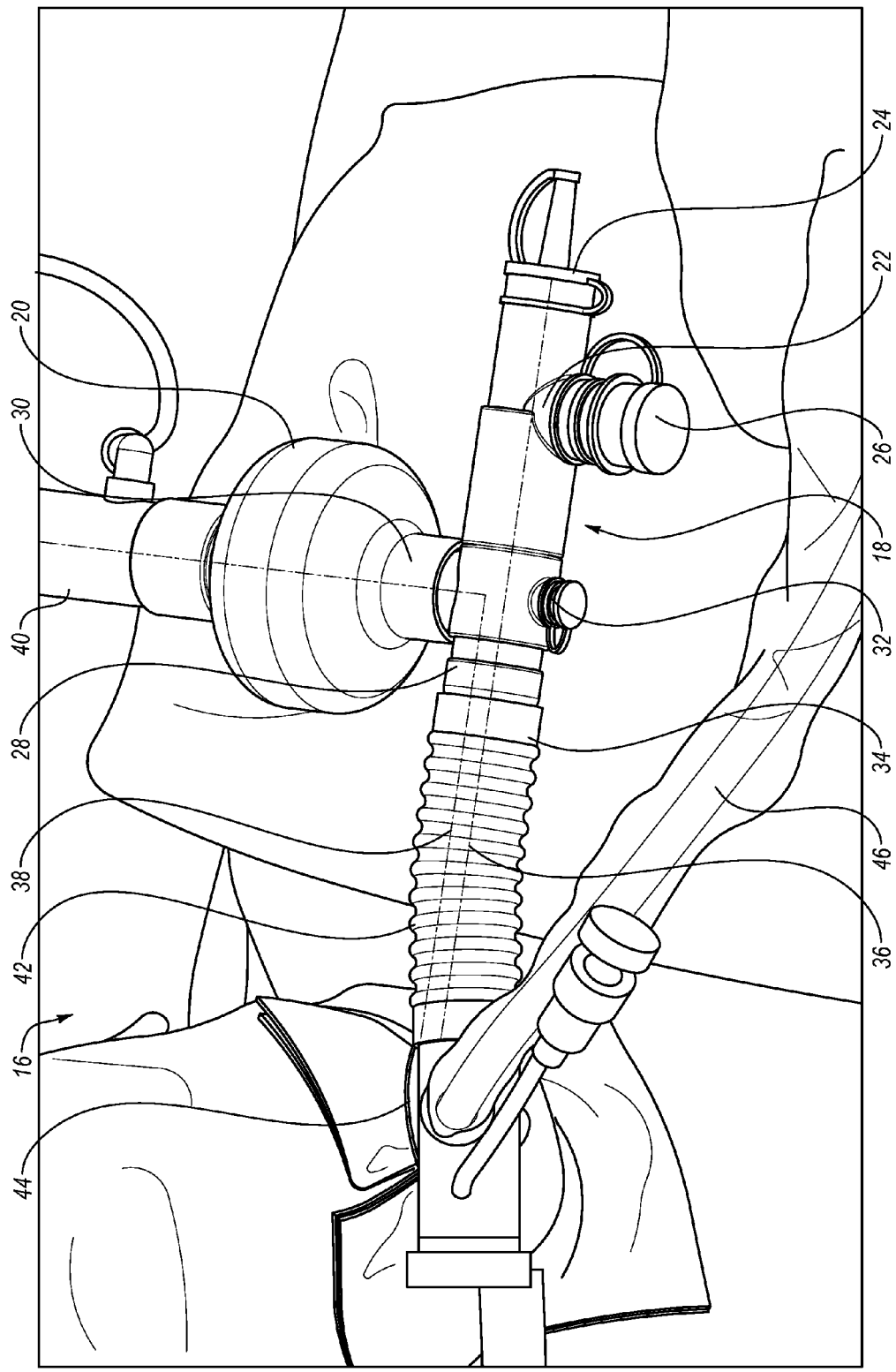
FIG. 4 is a perspective view of the tracheal humidification device of FIG. 3 attached to a patient.

In some embodiments, the body 18 may act as a collection chamber for collecting the secretions from a patient that may require suctioning. In some embodiments, the suction port 24 may be coupled with a suction device, such as, for example, a suction line, which may be used to remove the secretions from the body 18 or any other portion of the tracheal humidification device 16. In some embodiments, the suction line may be replaced at any time interval, such as, for example, when a secretion holding container to which the suction line is attached is full or at a time interval designated by a care facility. In some embodiments, the suction port 24 may be selectively opened to allow insertion of a suction device. In some embodiments, the suction port 24 may be disposed directly across from the tracheostomy connection port 34 to allow more effective suctioning of the secretions. For example, the suction port 24 may be disposed directly across from the tracheostomy connection port 34 to allow the suction device, which may be generally straight and/or rigid, to be inserted into the body 18 and easily reach all or substantially all of the secretion pathway 36, as illustrated in FIG. 4. In some embodiments, the suction port 24 may be disposed in a T-piece, which may be rotated such that the T-piece is inverted and points generally upwardly, preventing secretions from collecting in an arm of the T-piece outside of the secretion pathway 36. The various components, ports, features, etc. shown in FIG. 3 may be optional.

FIG. 4 is a perspective view of the tracheal humidification device 16 in use with a patient according to some embodiments. The first T-piece 22, for example, is arranged so that the nebulizer port 26 points generally away from the HME 20. Alternatively or additionally, the first T-piece 22 may be rotated so that the nebulizer port 26 is aligned with the HME 20. In this arrangement, for example, secretions may be less likely to flow into the nebulizer port 26. In some embodiments, the first T-piece 22 may be rotated so that the nebulizer port 26 of the first T-piece 22 is aligned with the HME 20 when the nebulizer port 26 is not in use. In some embodiments, the nebulizer port 26 may be aligned with the HME 20, for example, to allow a suction device coupled to and/or inserted in the suction port 24 to more effectively or more easily remove the secretions from the tracheal humidification device 16 as the secretions may be confined to the secretion pathway 36 and not accumulate in any downwardly pointing arms of the T-pieces. In some embodiments, secretions that accumulate in downwardly pointing arms of the T-pieces may be more difficult to reach using the suction device coupled to and/or inserted in the suction port 24. In some embodiments, the secretion pathway 36 may be substantially straight and easily suctioned using a suction device coupled to and/or inserted in the suction port 24. In some embodiments, when suctioning is not desired, the suction port 24 may be closed to prevent ambient air from entering the tracheal humidification device 16 and to maintain the closed system.

In some embodiments, the nebulizer port 26 may be coupled to a nebulizer. In some embodiments, the nebulizer port 26 may be disposed in a T-piece of the body 18 that may be rotated generally downwardly when the nebulizer is coupled to the nebulizer port 26. The nebulizer port 26 may include a spring-loaded valve into which a nebulizer may be inserted. When the nebulizer is removed from the spring-loaded valve, the valve may automatically close, maintaining the integrity of the closed system. In some embodiments, the nebulizer may be used, for example, to administer one or more medications to the patient through the tracheal humidification device 16. Further, in some embodiments, the nebulizer may be used, for example, as an air compressor to supplement the humidification provided by the HME 20 or similar device.

In some embodiments, the tracheal humidification device 16 may include the HME 20. While various embodiments described herein include an HME, an HCH or other similar device capable of acting as a filter and/or heat and moisture exchanger may be used. In some embodiments, the HME 20 may be coupled to the HME port 30. In some embodiments, the HME 20 may be coupled in a manner that allows it to be easily replaced, such as by fitting, threading, snapping, twisting, sliding, screwing, or the like. In some embodiments, the HME 20 may be replaced at various time intervals, such as, for example, daily, twice-daily, every other day, etc. In some embodiments, the HME 20 may capture heat and/or moisture on a patient's expiration and return it to the patient on the patient's subsequent inspiration. In some embodiments, the HME 20 may also filter particles from the air as the patient inhales, protecting the patient from dust, bacteria, harmful particles, etc.

As illustrated in FIG. 4, in some embodiments, the HME 20 may be disposed outside the secretion pathway 36. For example, the secretion pathway 36 may include different pathway portions from a breathing pathway 38, which may, for example, prevent secretions from entering the HME 20. In some embodiments, during use, the HME 20 may be disposed above the secretion pathway 36, and gravity may prevent the secretions from entering the HME 20. In some embodiments, the HME 20 may extend generally upwardly from an upwardly extending arm of a T-piece, such as, for example, the second T-piece 28. In some embodiments, the HME 20 may be generally vertically oriented. In some embodiments, the second T-piece 28 may be rotated with respect to the first T-piece 22 such that the HME 20 is disposed away from the patient's face. In some embodiments, a proximal arm of the second T-piece 28 may be longer than a distal arm of the second T-piece 28 in order to increase the distance of the HME 20 from the patient's face.

In some embodiments, the tracheal humidification device 16 may include an oxygen inlet port 40, which may be disposed in an upper opening of the HME 20. In some embodiments, some patients may require supplemental oxygen, and a supplemental oxygen device or oxygen supply tube may be connected to the oxygen inlet port 40. In some embodiments, supplemental oxygen may be administered to the patient via the HME 20. In some embodiments, the oxygen may pass through the HME 20 before entering the body of the tracheal humidification device 16 and reaching the patient. In some embodiments, the tracheal humidification device 16 may, however, reduce a patient's need for supplemental oxygen as it may increase breathing resistance and restore Positive End Expiratory Pressure (PEEP) lost by the patient's lungs. In some embodiments, the oxygen inlet port 40 may be part of the breathing pathway 38; hence, in some embodiments, when the patient inhales, ambient air and supplemental oxygen from the supplemental oxygen device may flow through the oxygen inlet port 40, through the HME 20, into the body 18, and through the tracheostomy connection port 34 to the patient. In some embodiments, air exhaled by the patient may travel along the breathing pathway 38 through the tracheostomy connection port 34, into the body 18, through the HME 20, and through the oxygen inlet port 40 into the ambient air.

In some embodiments, the monitoring port 32 may be coupled to a temperature monitoring device, a carbon dioxide monitoring device, and/or other monitoring device. In some embodiments, the monitoring port 32 may be disposed on a body of the second T-piece 28. In some embodiments, the monitoring port 32 may be located on an upper portion of the body 18 or a generally upwardly extending arm of a T-piece of the body 18, so that the secretions do not collect in the monitoring port 32, which may, for example, make it harder to remove the secretions with a suction device and/or creating potential for the secretions to leak out of the monitoring port 32.

In some embodiments, the tracheostomy connection port 34 may be coupled to a tracheostomy connection tube 42. As illustrated in FIG. 4, the tracheostomy connection tube 42 may be coupled to and/or integrally formed with an attachment piece 44, which may be attached directly to the tracheostomy. The tracheostomy connection tube 42 may be relatively short in length, such as, for example, six (6) inches. In some embodiments, the tracheostomy connection tube 42 may be relatively short to minimize dead space. In some embodiments, the tracheostomy connection tube 42 may allow the HME 20 to be disposed away from the patient's face and/or body. In some embodiments, the tracheostomy connection tube 42 may be flexible and/or corrugated to protect the tracheostomy from jerking. The tracheostomy connection tube 42 may be, for example, large bore tubing. In some embodiments, the attachment piece 44 may have a generally T-shaped configuration. A standard closed suction system 46 may be coupled to the attachment piece 44 to allow suctioning of the patient's tracheostomy tube. The standard closed suction system 46 may include, for example, a Kimberly-Clark KIMVENT Closed Suction System or similar closed suction system.

The suction port 24, the nebulizer port 26, the HME port 30, the monitoring port 32, the tracheostomy connection port 34, and/or the oxygen inlet port 40 may be selectively coupled to a corresponding device, such as, for example, a suction device, a nebulizer, an HME 20 or similar device, a monitoring device, a tracheostomy connection device, and/or the HME 20 or similar device. In some embodiments, the corresponding devices may be coupled to the one or more ports by fitting, threading, snapping, twisting, sliding, screwing, or the like. Further, the corresponding devices may be coupled to the one or more ports by, for example, a spring-loaded valve or the like.

As illustrated in FIG. 4, in some embodiments, the tracheal humidification device 16 may gently rest on one shoulder of the patient. In some embodiments, the tracheal humidification device 16 may be relatively small, compact, and/or highly portable.

Figure 5:
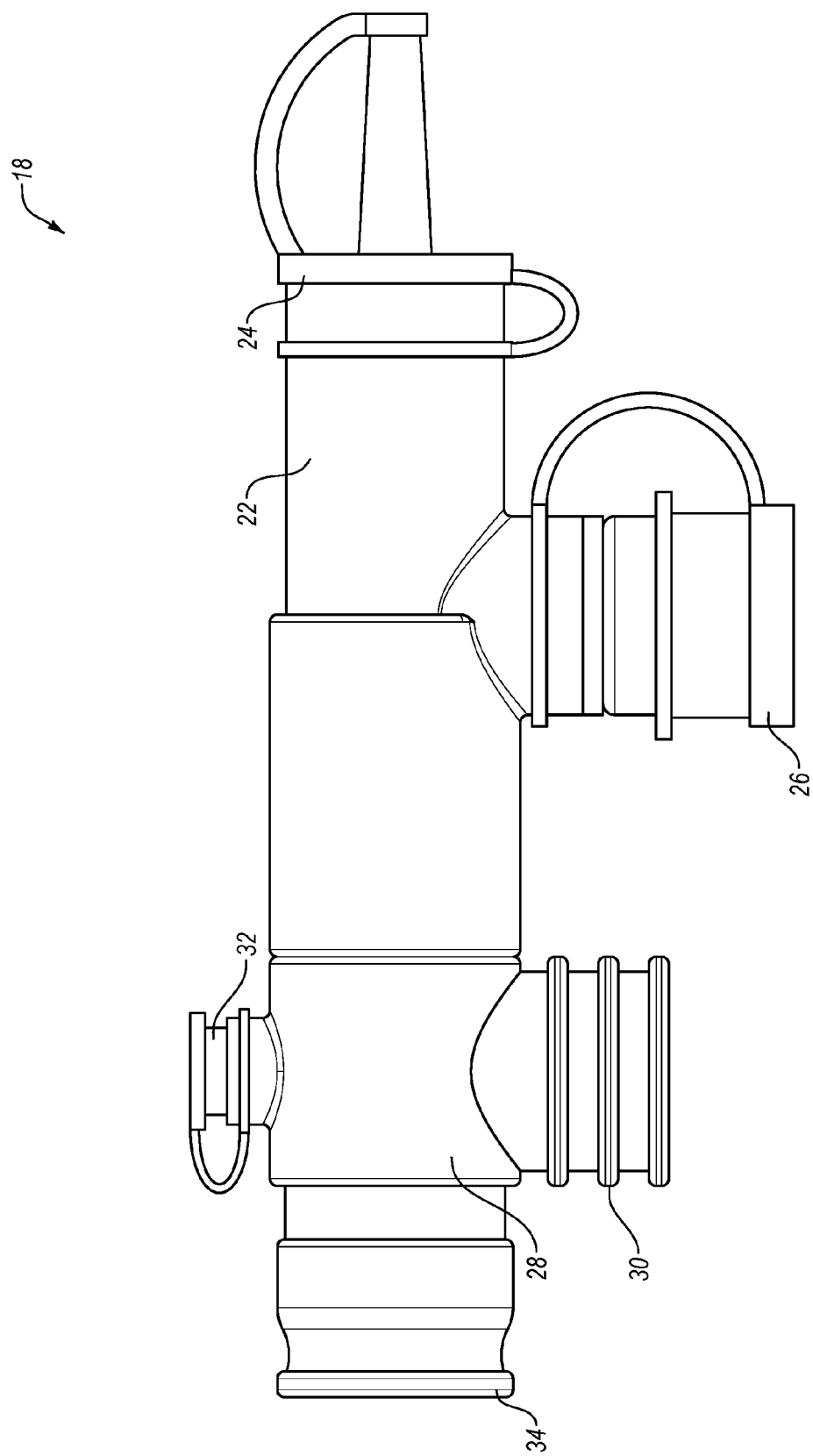
FIG. 5 is an enlarged perspective view of a body of the tracheal humidification device of FIG. 3.

FIG. 5 illustrates an enlarged perspective view of the body 18 of the tracheal humidification device 16. As illustrated in FIG. 5, the first T-piece 22 and the second T-piece 28 may be coupled to one another and may be rotatable with respect to each other such that the HME port 30 on the second T-piece 28 and the nebulizer port 26 on the first T-piece 22 generally point in the same direction.

Figure 6:
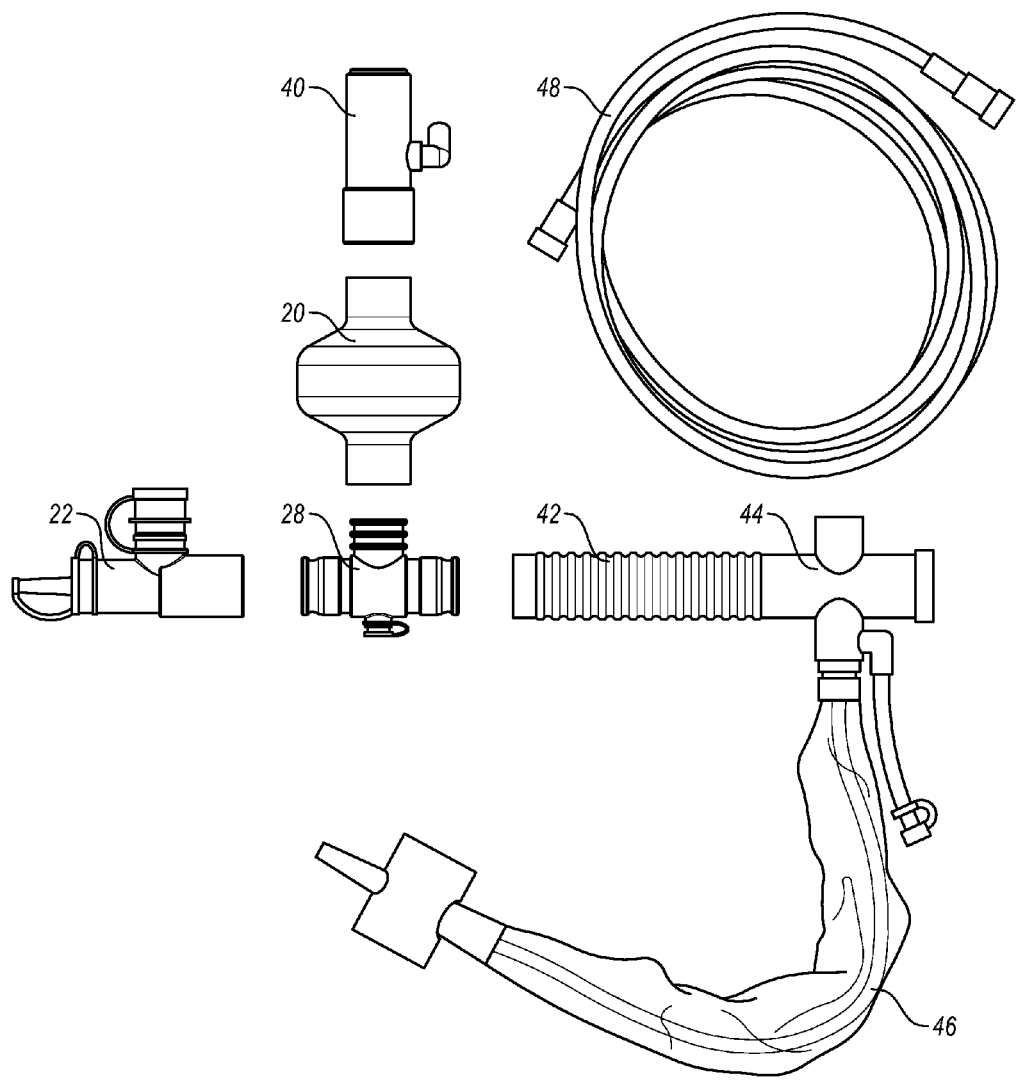
FIG. 6 illustrates one or more example components of the tracheal humidification device of FIG. 3.

FIG. 6 illustrates one or more example components of the tracheal humidification device 16. The tracheal humidification device 16 may include a first T-piece 22, which may be coupled to the second T-piece 28. The tracheal humidification device 16 may also include an HME 20, which may be coupled to an oxygen inlet port 40. The oxygen inlet port 40 may be coupled to an oxygen supply tube 48. The second T-piece 28 may be coupled to the tracheostomy connection tube 42, which may be coupled to the attachment piece 44. FIG. 6 also illustrates the standard closed suction system 46. In some embodiments, one or more of the components may be easily replaceable and/or disposable.

Figure 7:
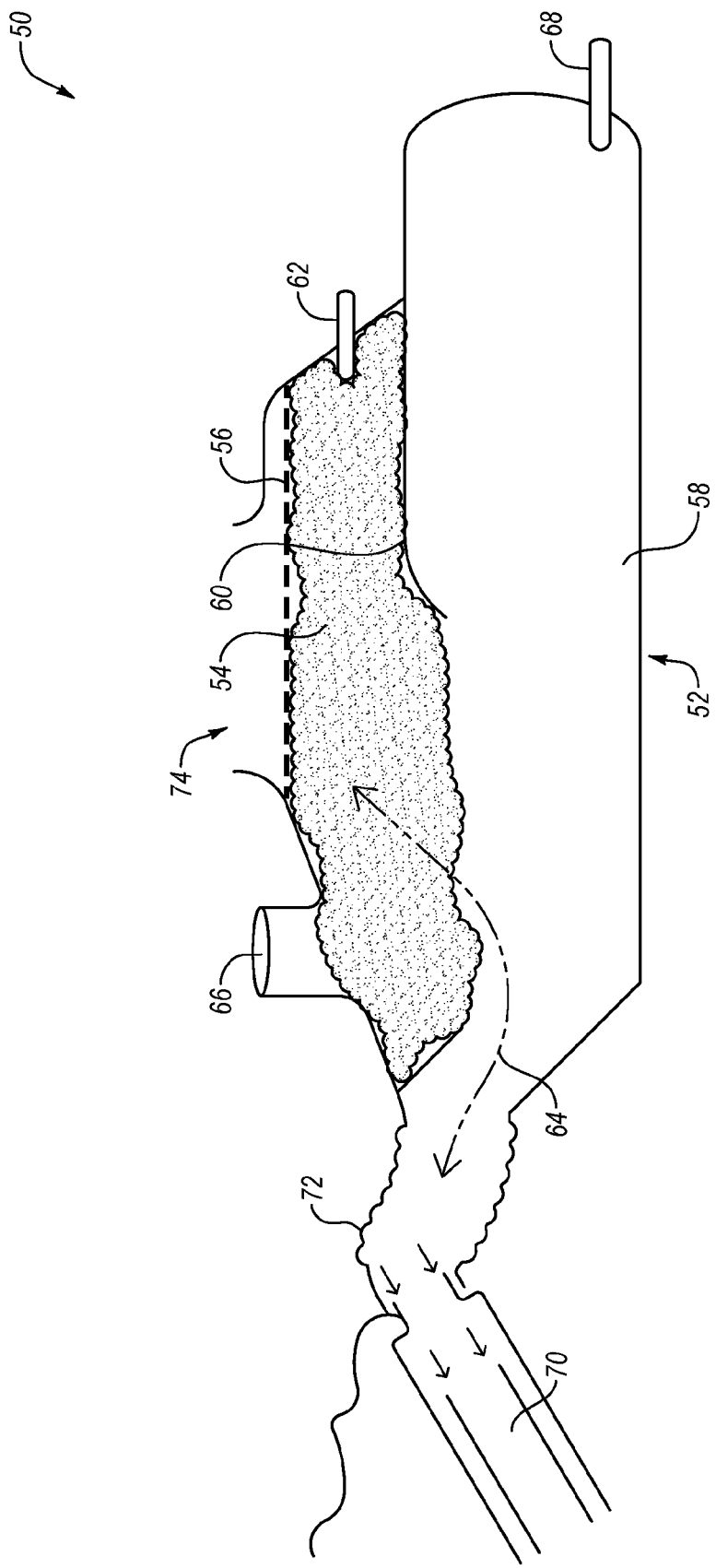
FIG. 7 is a cross-sectional view of another example tracheal humidification device.

Another example tracheal humidification device 50 is shown in FIG. 7. In some embodiments, the tracheal humidification device 50 may include a body 52. One or more aspects of an HME or similar device may be incorporated in a region of the body 52. For example, the body 52 may include an HME sponge 54. The HME sponge 54 may include foam, paper, or a substance that may act as a condensation and/or absorption surface. The HME sponge 54 may be disposed beneath a bacteria membrane 56, which may be disposed on an upper portion of the body 52 and/or within an opening 74 that may allow for inhalation and exhalation. In some embodiments, the HME sponge 54 and bacteria membrane 56 may be coupled together and may be removable and/or disposable.

The HME sponge 54 may be disposed above a secretion tray 58 of the body 52. The secretion tray 58 may be at least partially separated from an upper portion of the body 52 by a barrier 60. The upper portion of the body 52 may include or be coupled to an oxygen inlet port 62, which may be disposed above the secretion tray 58 and/or at least proximate to the HME sponge 54. In some embodiments, the oxygen include port may include a removable cap. While secretions may collect in the secretion tray 58, which may be disposed in a lower portion of the body 52, a breathing pathway 64 located primarily in the upper portion of the body 52, may remain substantially free of secretions. A nebulizer port 66 may be disposed above the breathing pathway 64 and may extend generally upwardly from the body 52. The nebulizer port 66 may include a closable cap that may include a spring-loaded valve that is sized and formed to fit with a standard nebulizer.

The secretion tray 58 may include a suction port 68 that may be used in conjunction with a vacuum or suction device for easy removal of secretions. The suction port 68 may be disposed on a distal end of the body 52. A proximal end of the body 52 may include or be coupled to a tracheostomy connection tube 70 and/or with a flex tube 72. The body 52, oxygen inlet port 62, nebulizer port 66, suction port 68, and/or tracheostomy connection tube 70 may correspond to the body 18, oxygen inlet port 40, nebulizer port 26, suction port 24, and/or tracheostomy connection tube 42 respectively as described with respect to FIGS. 3 to 6 and/or may include various characters and/or features of these components as described above.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

The use of "adapted to" or "configured to" is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

What is claimed is:

1. A tracheal humidification device comprising:
    a body portion comprising:
        a tracheostomy connection port formed to couple with a tracheostomy connection tube;
        a nebulizer port formed to couple with a nebulizer and having a closable seal that is closable when the nebulizer is not coupled with the nebulizer port; and
        a sealable oxygen port formed to couple with a supplemental oxygen device; and
    a heat moist exchanger device disposed within a region of the body portion and positioned to cover both the nebulizer port and the oxygen port when the nebulizer is coupled to the nebulizer port.

2. The tracheal humidification device according to claim 1, wherein the tracheal humidification device comprises a closed system when coupled with the tracheostomy connection tube.

3. The tracheal humidification device according to claim 1, wherein the nebulizer port comprises a spring-loaded valve.

4. The tracheal humidification device according to claim 1, wherein the nebulizer port extends upwardly from the body portion.

5. The tracheal humidification device according to claim 1, wherein the nebulizer port is disposed above a breathing pathway through the body portion.

6. The tracheal humidification device according to claim 1, wherein the body portion further comprises a secretion tray in a lower portion of the body portion.

7. The tracheal humidification device according to claim 6, wherein the secretion tray includes a suction port at an end opposite of the tracheostomy connection port.

8. The tracheal humidification device according to claim 6, wherein the body portion includes a breathing pathway above the secretion tray.

9. The tracheal humidification device according to claim 6, wherein the heat moist exchanger device is disposed completely above the secretion tray.

10. The tracheal humidification device according to claim 6, further comprising a barrier between the secretion tray and at least a portion of the heat moist exchanger device.

11. The tracheal humidification device according to claim 10, wherein the barrier includes a curved portion extending towards the secretion tray.

12. The tracheal humidification device according to claim 1, wherein the heat moist exchanger device is configured to act as a condensation and absorption surface.

13. The tracheal humidification device according to claim 1, wherein the heat moist exchanger device is manufactured from a sponge, foam, or paper.

14. The tracheal humidification device according to claim 1, further comprising a bacterial membrane disposed proximate the heat moist exchanger device.

15. The tracheal humidification device according to claim 14, wherein the bacterial membrane is physically coupled to the heat moist exchanger device.

16. The tracheal humidification device according to claim 15, wherein the bacterial membrane physically coupled with the heat moist exchanger device is removable from the body portion.

17. The tracheal humidification device according to claim 14, wherein the bacterial membrane is disposed within an opening in the body portion.

* * * * *